United States Patent [19]
Valenti et al.

[11] Patent Number: 5,869,446
[45] Date of Patent: Feb. 9, 1999

[54] PREPARATION OF LACTOFERRIN (OR SEROTRANSFERRIN OR OVOTRANSFERRIN) AND DESFERRIOXAMINE METHANESULFONATE (OR OTHER LOW MOLECULAR WEIGHT METAL ION CHELATORS) FOR THE THERAPY OF VIRAL INFECTIONS

[75] Inventors: Piera Valenti, Rome; Giovanni Antonini, Caprarola, both of Italy

[73] Assignee: Gambit International Limited, Tortola, Virgin Islands (Br.)

[21] Appl. No.: 924,882

[22] Filed: Sep. 5, 1997

Related U.S. Application Data

[63] Continuation-in-part of Ser. No. 677,594, Jul. 9, 1996, abandoned.

[51] Int. Cl.⁶ .................................... A61K 38/14
[52] U.S. Cl. .................. 514/8; 514/12; 514/13; 514/934; 558/40; 558/152
[58] Field of Search ................. 514/12, 13, 8, 514/934; 558/152, 40

[56] References Cited

U.S. PATENT DOCUMENTS

| | | | |
|---|---|---|---|
| 4,628,063 | 12/1986 | Haines et al. | 514/626 |
| 4,757,088 | 7/1988 | Haines et al. | 514/563 |
| 4,914,131 | 4/1990 | Haines et al. | 514/626 |
| 5,194,654 | 3/1993 | Hostetler et al. | 558/152 |
| 5,463,092 | 10/1995 | Hostetler et al. | 554/40 |

FOREIGN PATENT DOCUMENTS

| | | |
|---|---|---|
| 559425 | 3/1993 | European Pat. Off. . |
| 584558 | 7/1993 | European Pat. Off. . |
| 01233226-A | of 1989 | Japan . |
| 02233619-A | of 1989 | Japan . |
| 9318061 | 3/1992 | WIPO . |

OTHER PUBLICATIONS

Fujihara, et al., Lactoferrin inhibits herpes simplex virus type–1 (HSV–1) infection to mouse corea, Arch. Virol. 140: 1469–1472, 1995.

Polatnick et al., Effect of Zinc and Other Chemical Agents on Foot–and–Mouth Disease Virus Replication, Antimicrobial Agents and Chemotherapy, vol. 13, No. 5, pp. 731–734, May 1978.

Rohde, et al. Hydroxyquinolines Inhibit Ribonucleic Acid–Dependent Deoxyribonucleic Acid Polymerase and Inactivate Rous Sarcoma Virus and Herpes Simplex Virus, Antimicrobial Agents Chemotherapy, vol. 10, No. 2, pp. 234–240, 1976.

Lactoferrin: a Multifunctional Immunioregulatory Protein? (Brock, Jeremy) (1994).

Inhibition with Lactoferrin of Invitro Infection with Human Herpes Virus (Hasegawa, K. et al.) (1994).

Invitro Inhibition of Human Cytomegalovirus . . . (Antiviral Research) vol. 31, 1995 pp. 23–34.

Invitro Inhibition of Human Cytomegalovirus REplication 25 Antiviral Research 73–74 (1994).

*Primary Examiner*—Cecilia J. Tsang
*Assistant Examiner*—Bennett Celsa
*Attorney, Agent, or Firm*—Guido Modiano; Daniel J. O'Byrne

[57] ABSTRACT

A composition of lactoferrin, ovotransferrin or serotransferrin in combination with desferrioxamine methanesulfonate or other low molecular weight chelators for treating viral infections, and methods of treatment utilizing these compositions, is described.

13 Claims, No Drawings

1

PREPARATION OF LACTOFERRIN (OR SEROTRANSFERRIN OR OVOTRANSFERRIN) AND DESFERRIOXAMINE METHANESULFONATE (OR OTHER LOW MOLECULAR WEIGHT METAL ION CHELATORS) FOR THE THERAPY OF VIRAL INFECTIONS

This application is a cip of Ser. No. 08/677,594 filed Jul. 9, 1996 now abandoned.

TECHNICAL FIELD

The present invention relates to the therapeutic utilization of a preparation of lactoferrin (or analogous proteins like ovotransferrin and serotransferrin) in association with the iron chelator desferrioxamine methanesulfonate (or other low molecular weight metal ion chelators) for treating viral infectious diseases in humans.

BRIEF DESCRIPTION OF THE INVENTION

The present invention relates to the therapeutic utilization of the preparation of lactoferrin (and ovotransferrin and serotransferrin) and desferrioxamine methanesulphonate or other low molecular weight metal ion chelators such as 8-hydroxyquinoline and 1,10-phenanthroline for the therapy of acute or recurrent viral infectious diseases in humans. The present invention demonstrates the antiviral activity of such preparations based on the inhibition of both the absorption and the replication of several viruses. This antiviral activity is well evident towards a DNA virus, like Herpesviruses type 1 and 2 and towards an RNA virus, like Rhinovirus, and can be utilized for the therapy of acute or recurrent viral infections concerning the skin and mucosas. The antiviral activity is exerted by such materials in the presence and in the absence of metal ions such as iron, zinc and manganese chelated either by transferrins, by low molecular weight metal chelators or both.

BACKGROUND ART

It is known that viruses need the host's mechanisms of synthesis and energy to multiply themselves. It is also well known that the beginning of a viral infectious disease chiefly involves the adhesion of the viral particles to specific structures present on the membrane of the host cell. As a result of these early interactions, the intracellular phase of the virus and its subsequent replication or the integration in the cellular genome occurs.

When the virus multiplies, the host cell proceeds towards lysis and the infection spreads. In contrast, when the viral genome is integrated into the cell genome, avoiding the host defense, the host cell is not lysed as long as the viral genome remains integrated without multiplying. In particular cases, the integrated viral DNA can start a new replication cycle, causing cell lysis and, therefore, infections recur because of the production of mature viral particles. The peculiar life cycle of a virus does not easily allow one to find substances with antiviral properties that prevent the early phase of the interaction of virus-cells without being, at the same time, toxic towards the host cell.

Herpesviridae is a family of virus that cause acute and recurrent diseases. In particular, Herpes simplex virus type 1 (HSV1), a neurodermotrophic virus that afflicts 60–90% of the adult population and, after the primary infection, often becomes clinically silent in the host organism, and can remain in the skin cells and in the endings of nervous cells in a latent state. It is responsible for the events of primary gingival stomatitis, of recurrent labial Herpes, of eczema herpeticum,of herpetic keratitis and of supra-umbilical skin infections. In fact, after skin-breaking events like exposure to sunlight, fever or emotional stress, the virus can reactivate and cause the appearance of painful and boring skin vesicles that remain for some days even when after the disappearance of the skin-breaking event. Preferential sites of localization are lips and rarely genitals, contrary to that observed with Herpes simplex virus type 2 which is responsible for genital infections.These infections involve the genitalia, anorectum and oropharynx. A large study of patients with genital herpes suggested that recurrences typically occur 5–8 times a year.

Only sunlight filters are used for the prevention towards Herpes simples type 1 on the lips, while the antiviral therapy is based on chemotherapeutics that inhibit the viral replication of the Herpes simplex virus. However, the filters only prevent the viral reactivation after sunlight exposure and the chemotherapeutics are either potentially toxic and their prolonged use is often associated with serious effects such as anemia, neutropenia and irreversible testicular damage.

Another example is represented by Rhinovirus, ethiological agents of the common cold, for which a decisive therapy does not exist because of the 115 different antigenic varieties that exist which prevents the formulation of an effective vaccine. On the other hand, the relative harmlessness of the above mentioned viral infections does not suggest the therapeutic utilization of antiviral drugs even though they possess some toxicity towards the host organism.

With the aim to inhibit the viral replication, an approach can be represented by the inhibition of the early virus-cell interactions thus inhibiting the internalization of the infectious agent or by the inactivation of the enzymes necessary for viral replication.

Concerning the first approach, that is the inhibition of the early virus-cell interactions, many substances have been tested in the last years but only some of them carry this activity through specific bonds both to cell receptors and to viral anti-receptors.

Recently, an antiviral function of lactoferrin has been demonstrated, a glycoprotein able to bind 2 atoms of $Fe^{3+}$ per molecule. The antiviral function of lactoferrin, firstly attributed to its iron deprivation capability, may be, on the contrary, due to a specific binding with the host surface in its N-terminus in a region distinct from ther iron binding sites. In fact, it has been demonstrated that lactoferrin (human and bovine) specifically binds to heparin sulfate, a ubiquitous proteoglycan, multifunctional constituent of mammalian cell membranes and of extracellular matrix. This component and other glycosaminoglycans may act as receptors for some enveloped viruses, including HSV1 and HIV. It can be inferred that lactoferrin is able to selectively inhibit the early interactions HSV1-host cell and, consequently, is able to inhibit the internalization of the virus.

In physiological conditions, such as in the common media for cell cultures, lactoferrin is partially saturated in its iron binding sites. In this condition, lactoferrin assumes a "close" conformation that allows the binding to the surface receptorial structures of the host cells and a greater resistance to the proteases. This binding between saturated lactoferrin and the receptor, while competitively inhibiting the adsorption of the virus to the cell, facilitates the penetration of $Fe^{3+}$ ions inside the cell. The latter event could prevent a therapeutic utilization of lactoferrin as antiviral agent, since the iron transported into the cell influences the replication of the virus particles already present inside the cells. In fact, even with different viruses and experimental models and sometimes with conflicting results, it is well demonstrated that iron and other metals are important in the catalytic activity of viral ribonucleotide reductase enzymes. In fact, metal chelating substances are reported to be inhibitors of viral ribonucleotide reductases including those codified by Herpesviris, while they do not influence cellular reductases.

Among the above-stated chelators, desferrioxamine methariesulfonate, a hydroxamic siderophore produced by *Streptomyces pilosus* and for a long time utilized in the therapy of human hemochromatosis following hemolytic diseases, appears to be very active, being able to chelate $Fe^{3+}$ ions with high affinity and, with lower affinity, other metal ions.

The therapeutic utilization of these chelating compounds either in apo or different saturated forms as antiviral agents alone was, until now, not possible since the above-mentioned substances, while slowing down the viral multiplication phase, did not prevent the penetration of the virus into the cell. The cells would therefore be infected by the virus, anyhow.

The therapeutic model, described in the present invention is based on the synergistic antiviral activity exerted by lactoferrin (or serotransferrin or ovotransferrin) and desferrioxamine methanesulfonate (or other low molecular weight metal ion chelators) both compounds being in apo form or in iron, manganese and zinc saturated forms. The antiviral activity of this preparation, heretofore not described in literature, is remarkably higher than that shown with the two separate components because their activity is exerted on two separate phases of the viral cycle (adsorption and replication). Therefore, it can be inferred that therapeutic advantage of such a preparation is greater towards viral infections in comparison with the currently used antiviral pharmacological therapies based on the inhibition of viral replicative mechanisms and that are characterized by toxicity towards the host organism.

Lactoferrin, possessing very low or no toxicity, and the chelate desferrioxamine methanesulfonate, already utilized in human hemochromatosis therapy, can be administered by topical and systemic routes against viral infections concerning skin and mucous membranes such as nasal, oropharyngeal, intestinal, bronchial and genital membranes0.

DISCLOSURE OF THE INVENTION

An object of the present invention is the preparation constituted by lactoferrin, and, in a more general way, by serotransferrin or ovotransferrin, and by metal ion chelating substances such as desferrioxamine methanesulfonate or others, both compounds being in apo or iron, manganese and zinc saturated forms, the antiviral activity of which is demonstrated as being exerted through an inhibition of adsorption and replication of some viruses, and can be therapeutically utilized.

It will be shown that the antiviral activity towards DNA and RNA virus, exerted by the preparation of lactoferrin (or serotransferrin or ovotransferrin) and desferrioxamine methanesulfonate (or other low molecular weight metal ion chelators) both compounds being in apo or iron, manganese and zinc saturated forms behavesby the protecting against cell lysis due to viral multiplication of Herpes simplex type 1 and type 2 (chosen as DNA virus) and Rhinovirus (chosen as RNA virus). The antiviral activity of the preparation of lactoferrin (or serotransferrin or ovotransferrin) and desferrioxamine methanesulfonate (or other low molecular weight metal ion chelators) both compounds being in apo or iron, manganese and zinc saturated forms, so far not described in literature, is made evident by the reduced presence or absence of lysis plaques when the virus is added to cells cultured in the presence of this preparation. Since the antiviral activity of these preparations is exerted towards both HSV1 and HSV2 and Rhinovirus, the possibility of an utilization of these preparations for treating the acute or recurrent infections caused by these virus is contemplated.

Lactoferrin is a glycoprotein present in milk, in many biological secretions and in the granules of mammalian neutrophile leucocytes. Lactoferrin possesses an isoelectric point of 7.8, a molecular weight of about 83,100 and possesses two sugar chains containing 7–10% carbohydrates of total weight. Lactoferrin is known to bind 2 atoms of $Fe^{3+}$ per molecule, and is able to chelate other low molecular weight metal ions with different affinity. Its known function is to control the amount of free iron in biological liquids, inhibiting the bacterial growth (the bacteriostatic property is already well known) and decreasing the risk of free radicals formation catalyzed by the presence of uncoordinated iron. Lactoferrin belongs to a class of glycoproteins generally called "Transferrins", characterized by the presence of two binding sites for $Fe^{3+}$ and by a high degree (about 70%) of amino acid homology among them. Ovotransferrin and serotransferrin also belong to the class of "Transferrins".

Lactoferrin can be produced in large amounts by extraction from bovine milk. In the experiments described in the present invention bovine lactoferrin was mainly used but the same antiviral activity is exerted by all the proteins known as lactoferrin now on market, such as human lactoferrin and lactoferrin from the mouse, produced by extraction or utilizing recombinant DNA technique, and, therefore, the antiviral activity in preparation with metal ion chelators is extended, as described in the present invention, to all the lactoferrins from various sources and produced in any way.

The antiviral activity towards the above-mentioned viruses exerted by the preparation of lactoferrin and desferrioxamine methanesulfonate (or other low molecular weight metal ion chelators), both compounds being in apo or iron, manganese and zinc saturated forms, described in the present invention, is present, even if with a somewhat lower activity, by replacing lactoferrin with serotransferrin or ovotransferrin.

Furthermore, different $Fe^{3+}$, $Mn^{2+}$ and $Zn^{2+}$ saturation degrees of the above glycoproteins were tested, from the apo form to completely metal saturated forms. All transferrin preparations, although possessing different metal saturation degrees, have shown the antiviral activity when they were tested in preparation with desferrioxamine methanesulfonate or other low molecular weight metal ion chelators, both compounds being in the apo or metal saturated forms.

Desferrioxamine methanesulfonate is a metabolite produced by *Streptomyces pilosus* able to chelate one $Fe^{3+}$ per molecule in the extracellular and intracellular compartments. Chemically it belongs to the trihydroxamic siderophore class that, although it can bind with high affinity to $Fe^{3+}$ ions, show a good chelating capability towards other metal ions like $Al^{3}+$, Cu2+, Zn2+, $Mn^{2+}$ and $Co^{2+}$.

The antiviral activity of the actoferrin (or serotransferrin or ovotransferrin) compositions of the present invention showed no toxic concentrations of lactoferrin and desferrioxamine methanesulfonate towards different cell lines.

The antiviral activity towards HSV1 and HSV2 and Rhinovirus exerted by the preparation of lactoferrin (or serotransferrin or ovotransferrin) and desferrioxamine methanesulfonate (or other low molecular weight metal ion chelators) both compounds being in apo or iron, manganese and zinc saturated forms, is the main thrust of the present invention, and the general antiviral activity towards the viruses described in the present invention is not appreciably different whether the materials are from an extractive source or from other sources (i.e., from chemical synthesis) of lactoferrin (and ovotransferrin and serotransferrin) and desferrioxamine methanesulfonate or other low molecular weight metal chelators.

In the compositions according to the present invention, the transferrin may be represented by lactoferrin, ovotransferrin or serotransferrin, or by a mixture of these, and the low molecular weight metal chelators may be represented by desferrioxamine methanesulfonate, 8-hydroxyquinoline or by other metal ion chelators, having similar properties, or by a mixture of these, all the compounds being in the apo, or iron, manganese, and zinc saturated forms.

The compositions according to the present invention can have a variable weight ratio between the transferrin and the low molecular weight metal chelators, with the transferrin up to one thousand (or more) fold in excess with respect to the low molecular weight metal chelators or vice versa.

The compositions according to the present invention can be obtained and stored in liquid form, as solutions at a concentration of 0.1 to 10%, e.g., 1 to 5%, weight/volume (g/ml) of the mixture in solvents acceptable for pharmaceutical use, in particular water or hydro-alcholic solvents such as water-ethanol mixtures, or in solid form (lyophilized, dried, frozen) and in the other commonly known forms of storage; for example, immobilized or adsorbed on an inert support commonly used in the pharmaceutical field.

The compositions according to the invention, can thus be used in the liquid form, or in solid form, with the concentrations specified above.

The compositions according to the invention, can also comprise further conventional compounds as well as carriers, fillers, flavoring agents, preservatives, surfactants, colorants and other adjuvants selected from those conventionally used for the various liquid or solid form of preparations.

The formulation, according to the invention, can comprise antibacterial compounds such as quaternary ammonium compounds with one long alkyl chain on the nitrogen atom, alkali metal pyrophosphates and orthophosphates, halogenated bisphenols and halogenated diphenyl ethers, sodium benzoate, sodium salicylate, etc.

The formulation, according to the invention, can further comprise diluents, e.g. glycerin, propylene glycol, dioxalanes, glycerol, glycofurol, dimethylacetamide, ethyl lactate, alcohols, glycols,sorbitols, USP oils, NF oils, lecithin, lanolin, ethyl oleate, isopropyl myristate, benzyl benzoate, petrolatum, cocoa butter mixtures and gelifying substances, e.g., carboxyvinyl polymers, sodium alginate, agar, gelatin, cellulose derivatives, pectin, xanthan gum, polyvinyl pyrrolidone, glycerol, propylene glycol or polyethylene glycol.

The formulation, according to the invention, in either ointment, gel powder, or solution should be used for purposes of prevention of recurrent viral diseases, preferably twice a day. For the purpose of treatment the frequency of use can be increased to 3 to 4 times a day.

The preparation of lactoferrin (or serotransferrin or ovotransferrin) and desferrioxamine methanesulfonate (or other low molecular weight metal ion chelators) both compounds being in apo or iron, manganese and zinc saturated forms, has been tested for its antiviral activity towards HSV1 and HSV2, DNA pathogen virus, and towards Rhinovirus, RNA pathogen virus, through the inhibition of early phases of the adsorption and viral replication following an experimental model described below.

The utilization of the preparation of lactoferrin (or serotransferrin or ovotransferrin) and desferrioxamine methanesulfonate (or other low molecular weight metal ion chelators) both compounds being in apo or metal ion saturated forms in the therapy of infections by HSV1 and HSV2 and Rhinovirus is, therefore, only one of the possible therapeutic applications of the antiviral activity of such preparations as described in the present invention.

The examples shown below point out that the therapeutic antiviral activity towards these three viruses exerted by the preparation of lactoferrin (or serotransferrin or ovotransferrin or its analogous molecules) and desferrioxamine methanesulfonate (or other low molecular weight metal ion chelators) both compounds being in apo or iron,manganese and zinc saturated forms, described in the present invention, can be utilized in acute or recurrent viral infections and can be considered optimal as regards the presently used therapeutic treatments because it is characterized by very low or no toxicity.

The following examples were carried out on in vitro models that are universally considered valid for testing substances with antiviral activity. Moreover, an example is included of the antiviral activity of the lactoferrin and desferrioxamine methansulfonate carried out on mice.

EXAMPLES

Transferrins: both human lactoferrin and bovine lactoferrin were used in the following examples, except in the experiment showed in Table 6 in which only bovine lactoferrin was used. Serotransferrin in the text means human serotransferrin. Ovotransferrin in the text means hen's ovotransferrin.

Example 1

Cytotoxicity assay of transferrins and low molecular weight metal chelators.

A cytotoxicity test was initially carried out to evaluate the minimal toxic concentration of transferrins and of the low molecular weight metal chelators towards eucaryotic cells. Different concentrations of the tested substances were kept in contact with cell monolayers at 37° C. After 24 hours, the monolayers were examined by optical microscopy after vital staining. The cytotoxic effect was evaluated by examining the cell morphology and vitality.

TABLE 1

Assay of cytotoxicity of transferrins and low molecular weight metal chelators at different concentrations.

| Substances (mg/ml) | | Vero cells | HeLa cells |
| --- | --- | --- | --- |
| None | | – | – |
| Lactoferrin | 1 | – | – |
| Lactoferrin | 5 | – | – |
| Lactoferrin | 10 | – | – |
| Ovotransferrin | 1 | – | – |
| Ovotransferrin | 5 | – | – |
| Ovotransferrin | 10 | – | – |
| Serotransferrin | 1 | – | – |
| Serotransferrin | 5 | – | – |

TABLE 1-continued

Assay of cytotoxicity of transferrins and low molecular weight metal chelators at different concentrations.

| Substances (mg/ml) | | Vero cells | HeLa cells |
|---|---|---|---|
| Serotransferrin | 10 | − | − |
| Desferrioxamine | 0.01 | − | − |
| Desferrioxamine | 0.05 | − | − |
| Desferrioxamine | 0.1 | + | + |
| 8-hydroxyquinoline | 0.01 | − | − |
| 8-hydroxyquinoline | 0.05 | − | − |
| 8-hydroxyquinoline | 0.1 | + | + |

(−) no cytotoxic effect
(+) presence of cytotoxic effect

No differences were observed using the same compounds described in Table 1 in apo or iron, manganese, and zinc saturated forms.

Example 2

Antiviral activity of transferrins and low molecular weight metal chelators both in apo form and their influence on the early interactions between cell and HSV-1, HSV-2, and Rhinovirus.

We studied whether lactoferrin, serotransferrin, ovotransferrin and these low molecular weight metal chelators, at non- cytotoxic concentrations (see Table 1), inhibited the infection of Herpes virus 1 and 2 or Rhinovirus in vitro using Vero cell monolayers or HeLa cell monolayers respectively. The antiviral activity was determined by counting the number of plaques after infection in presence or in absence of the substance tested.

The utilized procedure was the following:

a) incubation at 4° C. for 1 h of lactoferrin (or serotransferrin or ovotransferrin or low molecular weight metal chelators) with cultured cells. After this period, the monolayer was washed and incubated at 37° C. to be infected with the virus;

b) incubation at 4° C. for 1 h of lactoferrin (or serotransferrin or ovotransferrin or low molecular weight metal chelators) with the tested virus. After the virus washing, the monolayer was incubated at 37° C. with fresh medium;

c) incubation at 4° C. for 1 h of lactoferrin (or serotransferrin or ovotransferrin or low molecular weight metal chelators) with the virus and the cell monolayer. After washing, fresh medium containing new lactoferrin (or serotransferrin or ovotransferrin or low molecular weight metal chelators) was added at 37° C.

The data concerning the activity of the transferrins and of the low molecular weight metal chelators are expressed as percentage of lysis plaques in comparison with the control in which the virus is incubated in their absence.

The utilized cells are different according with the tested virus. For testing Herpes simplex type 1 and 2, Vero cells were utilized, whereas for testing Rhinovirus we utilized HeLa cells. Both cell lines were cultured in MEM medium containing 1.2 g/l $NaCO_3$, 10% heat inactivated fetal calf serum, 100 U/ml penicillin, 100 mg/ml streptomycin. Transferrins were used at a concentration of 1 mg/ml, and the low molecular weight chelators at a concentration of 0.03 mg/ml.

TABLE 2

Effect of transferrins and low chelators both in apo-form on the early cell-virus interactions.

| | | Plaque forming units (%) | | |
|---|---|---|---|---|
| Conditions | | HSV1 | HSV2 | RHINOVIRUS |
| Control | | 100 | 100 | 100 |
| Human lactoferrin | a | 30 | 30 | 40 |
| | b | 10 | 10 | 20 |
| | c | 10 | 10 | 15 |
| Bovine lactoferrin | a | 10 | 10 | 20 |
| | b | 0 | 0 | 10 |
| | c | 0 | 0 | 5 |
| Ovotransferrin | a | 100 | 100 | 100 |
| | b | 100 | 100 | 100 |
| | c | 90 | 90 | 80 |
| Serotransferrin | a | 100 | 100 | 100 |
| | b | 90 | 100 | 100 |
| | c | 90 | 85 | 75 |
| Desferrioxamine methanesulfonate | a | 50 | 60 | 80 |
| | b | 100 | 100 | 100 |
| | c | 40 | 50 | 60 |
| 8-Hydroxyquinoline | a | 60 | 60 | 70 |
| | b | 100 | 100 | 100 |
| | c | 50 | 50 | 70 |

Bovine lactoferrin, in this experimental conditions, is demonstrated to be more active than human lactoferrin. On the contrary, serotransferrin or ovotransferrin shows a lesser antiviral activity.

As can be seen, concerning the inhibition of the early cell-virus interactions, desferrioxamine methanesulfonate, like 8-hydroxyquinoline, does not possess any activity (data reported in b).

Example 3

Antiviral activity of transferrins and low molecular weight metal chelators both in apo-forms on the replication of virus.

These experiments were performed by adding the transferrin and the low molecular weight metal chelators at 37° C. to the monolayer preincubated for 1 h at 4° C. in the presence of the tested virus. The data are reported in Table 3.

TABLE 3

Effect of transferrins and chelators on the replication of different viruses.

| | Plaque Forming Units (%) | | |
|---|---|---|---|
| Conditions | HSV1 | HSV2 | RHINOVIRUS |
| Control | 100 | 100 | 100 |
| Human lactoferrin | 100 | 100 | 100 |
| Bovine lactoferrin | 100 | 100 | 100 |
| Ovotransferrin | 100 | 100 | 100 |
| Serotransferrin | 100 | 100 | 100 |
| Desferrioxamine methanesulfonate | 80 | 80 | 90 |
| 8-Hydroxyquinoline | 80 | 80 | 90 |

From the reported data, it is evident that lactoferrin and other transferrins do not affect the intracellular phase and consequently the replication of the virus, contrary to that observed with desferrioxamine methanesulfonate and 8-hydroxyquinoline, which, for their well known effect of inhibiting the viral ribonucleotide reductase, reduce the number of plaque forming units.

Example 4

Antiviral activity of the transferrins and low molecular weight metal chelators preparation in apo form.

The maximum of the antiviral activity can be obtained when the substances (lactoferrin, serotransferrin or ovotransferrin and desferrioxamine methanesulfonate or 8-hydroxyquinoline) exert their action together, i.e., the inhibition of the virus-cell interaction by lactoferrin and the inhibition of intracellular replication by desferrioxamine methanesulfonate or 8-hydroxyquinoline.

The experimental procedure is described below:
a) incubation at 4° C. for 1 h of different preparations with cultured cells. After this period, the monolayer is washed and incubated at 37° C. to be infected with defined amounts of virus;
b) incubation at 4° C. for 1 h of the preparations with the tested virus and, subsequently, after the virus washing, the monolayer is incubated at 37° C.;
c) incubation at 4° C. for 1 h of the preparations with the virus and the cell monolayers. After washing, fresh medium containing newly the preparations was added at 37° C.

TABLE 4

Activity of the transferrins and low molecular weight metal chelators preparations in apo form.

| Conditions | | Plaque Forming Units (%) | | |
| --- | --- | --- | --- | --- |
| | | HSV1 | HSV2 | RHINOVIRUS |
| Control | | 100 | 100 | 100 |
| Bovine lactoferrin | a | 0 | 0 | 0 |
| +desferrioxamine methane-sulfonate | b | 0 | 0 | 0 |
| | c | 0 | 0 | 0 |
| Human lactoferrin | a | 0 | 0 | 0 |
| +desferrioxamine methane-sulfonate | b | 0 | 0 | 0 |
| | c | 0 | 0 | 0 |
| Serotransferrin | a | 40 | 50 | 50 |
| +desferrioxamine methane-sulfonate | b | 30 | 30 | 30 |
| | c | 10 | 10 | 10 |
| Ovotransferrin | a | 50 | 60 | 60 |
| +desferrioxamine methane-sulfonate | b | 30 | 30 | 30 |
| | c | 10 | 10 | 20 |
| Bovine lactoferrin +8-hydroxyquinoline | a | 0 | 0 | 0 |
| | b | 0 | 0 | 0 |
| | c | 0 | 0 | 0 |
| Human lactoferrin +8-hydroxyquinoline | a | 0 | 0 | 0 |
| | b | 0 | 0 | 0 |
| | c | 0 | 0 | 0 |
| Serotransferrin +8-hydroxyquinoline | a | 50 | 50 | 60 |
| | b | 30 | 30 | 30 |
| | c | 10 | 10 | 10 |
| Ovotransferrin +8-hydroxyquinoline | a | 60 | 60 | 50 |
| | b | 30 | 30 | 30 |
| | c | 10 | 10 | 10 |

It is thus evident that in all the experimental conditions the viral replication is inhibited by transferrins and it is maximal for the preparation of lactoferrin with desferrioxamine methanesulfonate or 8-hydroxyquinoline. Utilizing the transferrins and low molecular weight metal chelators together, it is possible to act both on the early interaction and on the intracellular replication, thus obtaining the maximum antiviral effect.

Example 5
Antiviral activity of lactoferrin and desferrioxamine methanesulfonate preparation in saturated forms.

Table 5 concerns the experiments carried out using the bovine lactoferrin and desferrioxamine methanesulfonate saturated with $Fe^{3+}$, $Zn^{2+}$ and $Mn^{2+}$. In order to verify the putative synergic effect, the lactoferrin was used at a concentration which shows a 50% of inhibition of plaque forming units such as 0.1 mg/ml. The chelators were used at a concentration of 30 μg/ml.

The experimental procedure is described below:
a) incubation at 4° C. for 1 h of different preparations with cultured cells. After this period, the monolayer was washed and incubated at 37° C. to be infected with definied amount of virus;
b) incubation at 4° C. for 1 h of the preparations with the tested virus and, subsequently, after the virus washing, the monolayer was incubated at 37° C. to be infected;
c) incubation at 4° C. for 1 h of the preparations with the virus and the cell monolayers. After washing, fresh medium containing newly the preparations was added at 37° C.

TABLE 5

Activity of the bovine lactoferrin-desferrioxamine methanesulfonate preparations in saturated forms

| Conditions | | Plaque Forming Units (%) | | |
| --- | --- | --- | --- | --- |
| | | HSV1 | HSV2 | RHINOVIRUS |
| Control | | 100 | 100 | 100 |
| Lactoferrin | a | 50 | 50 | 50 |
| +desferrioxamine methane-sulfonate | b | 60 | 60 | 60 |
| | c | 50 | 50 | 50 |
| Iron-lactoferrin | a | 30 | 30 | 30 |
| +desferrioxamine methane-sulfonate | b | 20 | 20 | 20 |
| | c | 10 | 10 | 10 |
| Iron-Lactoferrin | a | 0 | 0 | 0 |
| +iron desferriox. methane-sulfonate | b | 0 | 0 | 0 |
| | c | 0 | 0 | 0 |
| Mn-Lactoferrin | a | 20 | 0 | 0 |
| + desferriox.methane-sulfonate | b | 20 | 0 | 0 |
| | c | 10 | 0 | 0 |
| Mn-lactoferrin | a | 0 | 0 | 0 |
| +Mn desferriox. methane-sulfonate | b | 0 | 0 | 0 |
| | c | 0 | 0 | 0 |
| Zn-lactoferrin | a | 40 | 30 | 30 |
| +desferriox. methane-sulfonate | b | 30 | 20 | 20 |
| | c | 20 | 10 | 10 |
| Zn-lactoferrin | a | 0 | 0 | 0 |
| +Zndesferriox.methane-sulfonate | b | 0 | 0 | 0 |
| | c | 0 | 0 | 0 |

It is well evident that in all the experimental conditions the viral replication is maximally inhibited by lactoferrin and desferrioxamine methanesulfonate preparation when both substance are saturated with metal ions.

Results identical to those reported in Table 5, were obtained with human lactoferrin in saturated form. In contrast, lower antiviral activities were obtained by using serotransferrin and ovotransferrin, in saturated form, instead of lactoferrin. Results very similar to those shown in Table 5 were obtained by using 8-hydroxyquinoline, or 1,10-phenanthroline instead of desferrioxamine. Antiviral activities intermediate between those obtained with apo and metal saturated forms of transferrin and low molecular weight metal chelator were also observed by replacing iron, zinc and manganese with other metal ions like $Cu^{2+}$, $Co^{2+}$ and $Ni^{2+}$.

Example 6
In vivo activity of lactoferrin and desferrioxamine methanesulfonate preparation in apo or saturated forms We tested the inhibitory effect of the lactoferrin and desferrioxamine methanesulfonate compositions on HSV-1 infection in the mouse cornea in order to verify the data obtained in the in vitro models. The experiments were carried out utilizing as prototype the preparation constituted by 1% bovine lactoferrin and 0.1% desferrioxamine methanesulfonate administered in two different groups of HSV-1 infected mice. Both lactoferrin and desferrioxamine were used in apo form since it is known that they are able to become metal-saturated after being administered to humans and animals.

i) One group of mice started the instillation of 1% lactoferrin or 0.1% desferrioxamine methanesulfonate or 1% lactoferrin-0.1% desferrioxamine methanesulfonate eye drop 4 times starting at the time of infection;

ii) to the other group of mice was administered a solution of 1% lactoferrin or 0.1% desferrioxamine methanesulfonate or 1% lactoferrin-0.1% desferrioxamine methanesulfonate eye drop 4 times a day starting 24 h after HSV-1 infection.

Clinical signs were observed daily using a hand slit lamp. They developed epithelial keratitis on 2 days post infection. The eyes were excised at 24 h of infection and homogenized in order to determine the virus titre. The effect of the above described solutions was compared with those obtained by administering 2.5% acyclovir.

The data obtained are shown in Table 6 in which only the data obtained administering the substances at the time of infection are reported. The administration after the infection did not inhibit HSV-1 growth.

TABLE 6

Protective effect of preparation of bovine lactoferrin with desferrioxamine methanesulfonate on HSV-1 infection to mouse cornea.

| Substances administered | % Titers of HSV-1 (PFU/0.1 g eye) |
| --- | --- |
| None | 100 |
| 1% Lactoferrin | 30 |
| 0.1% Desferrioxamine | 90 |
| 1% Lactoferrin - 0.1% Desferrioxamine | 5 |
| 2.5% Acyclovir | 10 |

AS shown, topical administration the combination according to the invention results in more activity with-respect to lactoferrin or desferrioxamine methanesulfonate alone and reduced the viral titre of about 95%.

Example 7

Lyophilized powder
 Composition per 5 g
Active ingredients:
 Human lactoferrin, SIGMA Chemical Co., cat. L0520, 4.8 g
 Desferroxamine methanesulfonate, Ciba Geigy, 0.2 g
Use
 Dissolve into distilled water and inject i.m. once a day.

Example 8

Ointment
 Composition per 100 g
Active ingredients:
 Lactoferrin, from bovine milk, SIGMA Chemical Co., cat. L4765, 4.8 g
 Desferroxamine methanesulfonate, Ciba Geigy, 0.1 g
Carriers, preservatives agents:
 Paraffin oil 10 g
 Vaseline 80 g
Use
 Apply on the skin twice a day Example 9

Cream
 Composition per 100 g
Active ingredients:
 Lactoferrin, from bovine milk, SIGMA Chemical Co., cat. L4765, 4.8 g
 Desferroxamine methanesulfonate, Ciba Geigy, 0.1 g
Carriers, preservatives agents:
 Paraffin oil 6 g
 Chlorocresol 0.1 g
 Vaseline 15 g
 Ketostearyl alcohol 7.2 g
 Polyethylene glycol monocethyl ether 1.8 g
 Distilled water up to 100 g
Use
 Apply on the skin twice a day.

Example 10

Gel
 Composition per 100 g
Active ingredients:
 Lactoferrin, from bovine milk, SIGMA Chemical Co., cat. L4765, 4.8 g
 Desferroxamine methanesulfonate, Ciba Geigy, 0.1 g
Carriers, preservatives agents:

| Methyl-p-hydroxybenzoate | 100 mg |
| --- | --- |
| Propyl-p-hydroxybenzoate | 20 mg |
| Xanthan gum | 4 g |
| Lecithin | 3 g |
| Vitamin E | 100 mg |
| Distilled water up to | 100 g |

Use
 Apply on the skin twice a day.

Example 11

Spreading powder
 Composition per 100 g
Active ingredients:
 Lactoferrin, from bovine milk, SIGMA Chemical Co., cat. L4765, 4.8 g
 Desferroxamine methanesulfonate, Ciba Geigy, 0.1 g
Carriers, preservatives, agents:

| Glycine | 4 g |
| --- | --- |
| Zin oxide | 3.4 g |
| Corn starch | 80 g |
| Sodium metabisulfite | 100 mg |
| Silica | 1 g |

Use
 Spread on the skin twice a day

Example 12

Nasal spray
 Composition per 100 g
Active ingredients:
 Lactoferrin, from bovine milk, SIGMA Chemical Co., cat. L4765, 4.8 g
 Desferroxamine methanesulfonate, Ciba Geigy, 0.1 g
Carriers, preservatives agents:

| Methyl-p-hydroxybenzoate | 100 mg |
| --- | --- |
| Propyl-p-hydroxybenzoate | 20 mg |

-continued

| | |
|---|---|
| Sodium phosphate monobasic | 200 mg |
| Sodium EDTA | 50 mg |
| Distilled water up to | 100 g |

Use

Spray into the nostrils twice a day

Example 13

Nasal drops

Composition per 100 ml

Active inoredients:

Lactoferrin, from bovine milk, SIGMA Chemical Co., cat. L4765, 4.8 g

Desferroxamine methanesulfonate, Ciba Geigy, 0.1 g

Carriers, preservatives agents:

| | |
|---|---|
| Methyl-p-hydroxybenzoate | 100 mg |
| Propyl-p-hydroxybenzoate | 20 mg |
| Sodium chloride | 0.8 g |
| Distilled water up to | 100 ml |

Use

Drop 0.5 mls of solution per each nostril twice a day

We claim:

1. A composition having antiviral activity towards DNA/RNA virus comprising a transferrin selected from the group consisting of lactoferrin, ovotransferrin, serotransferrin and mixtures thereof, a low molecular weight metal ion chelator and a pharmaceutically acceptable carrier.

2. A composition according to claim 1, wherein said transferrin has a saturation degree which ranges from apo form to a completely metal saturated form.

3. A composition according to claim 2, wherein said metal is selected from the group consisting of iron, manganese, copper, nickel, cobalt, zinc and mixtures thereof.

4. A composition according to claim 1, wherein said metal ion chelator is selected from the group consisting of desferrioxamine methanesulfonate, 8-hydroxyquinolone, 1,10-phenanthroline and mixtures thereof.

5. A composition according to claim 1, wherein said metal ion chelator has a saturation degree which ranges from apo form to a completely metal saturated form.

6. A composition according to claim 5, wherein said metal is selected from the group consisting of iron, manganese, copper, nickel, cobalt, zinc and mixtures thereof.

7. A method for treating viral infectious diseases in a patient in need thereof including the administration to the patient of a therapeutically effective amount of a composition comprising a transferrin selected from the group consisting of lactoferrin, ovotransferrin, serotransferrin and mixtures thereof, a low molecular weight metal ion chelator and a pharmaceutically acceptable carrier.

8. A method according to claim 7, wherein said viral infectious diseases are caused by a virus selected from the group consisting of Herpes simplex virus type 1, Herpes simplex virus type 2, and Rhinovirus.

9. A method according to claim 7, wherein said transferrin has a saturation degree which ranges from apo form to a completely metal saturated form.

10. A method according to claim 7, wherein said metal is selected from the group consisting of iron, manganese, copper, nickel, cobalt, zinc and mixtures thereof.

11. A method according to claim 7, wherein said metal ion chelator is selected from the group consisting of desferrioxamine methanesulfonate, 8-hydroxyquinolone, 1,10-phenanthroline and mixtures thereof.

12. A method according to claim 7, wherein said transferrin has a saturation degree which ranges from apo form to a completely metal saturated form.

13. A method according to claim 12, wherein said metal is selected from the group consisting of iron, manganese, copper, nickel, cobalt, zinc and mixtures thereof.

* * * * *